United States Patent
Kim et al.

(10) Patent No.: US 11,230,703 B2
(45) Date of Patent: Jan. 25, 2022

(54) RECOMBINANT MICROORGANISM AND METHOD FOR PRODUCTION OF FORMIC ACID BY USING SAME

(71) Applicant: UNIST(ULSAN NATIONAL INSTITUTE OF SCIENCE AND TECHNOLOGY), Ulsan (KR)

(72) Inventors: Yong Hwan Kim, Ulsan (KR); Jung Ho Jang, Ulsan (KR); Byoung Wook Jeon, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 0 days.

(21) Appl. No.: 16/495,680

(22) PCT Filed: Nov. 14, 2018

(86) PCT No.: PCT/KR2018/013894
§ 371 (c)(1),
(2) Date: Sep. 19, 2019

(87) PCT Pub. No.: WO2019/098671
PCT Pub. Date: May 23, 2019

(65) Prior Publication Data
US 2020/0095620 A1    Mar. 26, 2020

(30) Foreign Application Priority Data
Nov. 15, 2017 (KR) .................... 10-2017-0152507

(51) Int. Cl.
*C12N 9/04* (2006.01)
*C12P 7/40* (2006.01)
*C12N 9/02* (2006.01)
*C12N 1/20* (2006.01)
*C12N 15/74* (2006.01)
*C12R 1/07* (2006.01)

(52) U.S. Cl.
CPC ............. *C12N 9/0008* (2013.01); *C12N 1/20* (2013.01); *C12N 1/205* (2021.05); *C12N 15/74* (2013.01); *C12P 7/40* (2013.01); *C12R 2001/07* (2021.05)

(58) Field of Classification Search
CPC .................................. C12N 9/0008; C12P 7/40
See application file for complete search history.

(56) References Cited

FOREIGN PATENT DOCUMENTS

KR    10-1524340    6/2015
KR    10-1655939    9/2016

(Continued)

OTHER PUBLICATIONS

Laukel. The tungsten-containing formate dehydrogenase from Methylobacterium extorquens AM1: Purification and properties. Eur. J. Biochem. 270, 325-333 (2003) _ FEBS 2003.*

(Continued)

*Primary Examiner* — Yong D Pak
(74) *Attorney, Agent, or Firm* — Klarquist Sparkman, LLP

(57) ABSTRACT

The present invention relates to a recombinant microorganism for producing formic acid, which has a formate dehydrogenase 1 alpha subunit (FDH1α)-encoding endogenous gene deleted therefrom and an FDH1-encoding exogenous gene introduced thereinto, and a method for production of formic acid by using the microorganism.

15 Claims, 10 Drawing Sheets
Specification includes a Sequence Listing.

(56) References Cited

FOREIGN PATENT DOCUMENTS

WO    WO 2015/064517    5/2015
WO    WO 2017/119731    7/2017

OTHER PUBLICATIONS

Chao. Overexpression of the methanol dehydrogenase gene mxaF in *Methylobacterium* sp. MB200 enhances L-serine production. Letters in Applied Microbiology 61, 390-396. 2015.*
Chistoserdova. Multiple Formate Dehydrogenase Enzymes in the Facultative Methylotroph Methylobacterium extorquens AM1 Are Dispensable for Growth on Methanol. Journal of Bacteriology. vol. 186, No. Jan. 1, 2004, p. 22-28.*
Marx. Development of improved versatile broad-hostrange vectors for use in methylotrophs and other Gram-negative bacteria. Microbiology (2001), 147, 2065-2075.*
Machine translation of KR 10-1655939. retrieved via google translate on Feb. 11, 2021.*
Machine translation of KR-10-152340. retrieved via google translate on Feb. 11, 2021.*
Kennedy et al., "Systems-Level Engineering of Nonfermentative Metabolism in Yeast," *Genetics*, vol. 183:385-397, 2009.
Laukel, et al., "The tungsten-containing formate dehydrogenase from *Methylobacterium extorquens* AMI: Purification and properties," *Eur. J. Biochem.*, vol. 270:325-333, 2003.
International Search Report and Written Opinion for PCT/KR2018/013894, dated Apr. 29, 2019 (with English translation of the International Search Report).

\* cited by examiner

A

B

RECOMBINANT MICROORGANISM AND METHOD FOR PRODUCTION OF FORMIC ACID BY USING SAME

CROSS REFERENCE TO RELATED APPLICATIONS

This is the U.S. National Stage of International Application No. PCT/KR2018/013894, filed Nov. 14, 2018, which claims the benefit of prior Korean Patent Application No. 10-2017-0152507, filed Nov. 15, 2017, which is incorporated herein in its entirety.

INCORPORATION OF SEQUENCE LISTING

The Sequence Listing is submitted as an ASCII text file, created on Sep. 17, 2019, 20.2 KB, which is incorporated by reference herein.

TECHNICAL FIELD

The present disclosure relates to a microorganism, specifically, a recombinant microorganism of the genus *Methylobacterium* having increased production of formate, from which an endogenous formate dehydrogenase 1 alpha subunit (fdh1α) gene is deleted and in which an exogenous fdh1 is expressed, and a method of preparing formate using the recombinant microorganism.

BACKGROUND ART

The rapid development of a wide range of industries using fossil fuels has led to drastically increased levels of atmospheric carbon dioxide [1]. Furthermore, a vast number of papers confirmed that elevated carbon dioxide levels in the atmosphere are a critical factor in global warming via greenhouse effects [1-3]. Therefore, conversion of carbon dioxide to value-added chemicals has been posited as an indispensable technology for slowing down the rate of atmospheric accumulation of carbon dioxide. Fortunately, carbon dioxide is a promising renewable source to produce environmentally friendly chemical platforms such as formate, dimethyl carbonate, polymers thereof, etc. [4].

Among many candidates that may be produced from carbon dioxide, formate is one of the most ideal chemicals in terms of economic and environmental benefits [5]. In particular, a direct formate fuel cell (DFFC) that converts formate to electrical energy has been suggested as a solution for renewable energy storage since energy generated from various renewable sources such as wind, solar, and hydro is able to be easily stored in formate. Additionally, formate is advantageous in that it is able to be safely transported, as compared with hydrogen gas, because formate is non-flammable, non-toxic, and inert in the environment [6, 7].

Despite the promising potential, existing technologies for converting carbon dioxide into valuable compounds harbor critical limitations such as harsh reaction conditions and requirements of rare precious metal catalysts and expensive reducing agents such as hydrogen gas, hydride, etc. [8, 9]. Even though electro-catalysis of carbon dioxide is a promising alternative in terms of relatively low electrical energy costs, some chemical electro-catalysts frequently demonstrate insufficient reaction selectivity during the conversion of carbon dioxide to formate due to the production of hydrogen gas as a by-product at a significant rate [10]. Accordingly, enzyme-based electro-catalyzed production of formate from carbon dioxide has received greater attention due to its exceptional selectivity for formate [11-14]. However, to render formate production from carbon dioxide feasible, effective oxygen-tolerant biocatalysts capable of directly using electrons supplied from a cathode are urgently needed [15].

In the petrochemical industry, a technology for supplying a C1 compound as a raw material is a very important basic step. This technology is called 'C1 chemistry', and in the field of C1 chemistry, attempts have been made to obtain C1 compounds from microorganisms because of limited petroleum fuel, as well as environmental and economic reasons. In the C1 chemistry, conversion of carbon dioxide to formate is recognized as a fundamental step in building C1 chemical platforms. Among numerous microorganisms for building C1 chemical platforms, *Methylobacterium extorquens* AM1 was reported to exhibit remarkable activity to convert carbon dioxide into formate. The present inventors have reported a novel approach for the conversion of carbon dioxide to formate through electro-catalysis using *Methylobacterium extorquens* AM1 as a whole-cell biocatalyst. The present inventors demonstrated that *Methylobacterium extorquens* AM1 has the ability to produce formate from carbon dioxide with high oxygen-stability in electrochemical reactors [16]. However, enzymes primarily responsible for the synthesis of formate from carbon dioxide remain unknown.

PRIOR ART DOCUMENTS

Non-Patent Documents (Non-Patent Document 1)1. PNAS, 2010, 107, 5687-5692.
(Non-Patent Document 2)2. PNAS, 2009, 106, 1704-1709.
(Non-Patent Document 3)3. Nature, 2009, 459, 829-U823.
(Non-Patent Document 4)4. Chem Rev, 2014, 114, 1709-1742.
(Non-Patent Document 5)5. Energy Environ. Sci., 2015, 8, 3283-3297.
(Non-Patent Document 6)6. ChemSusChem, 2015, 8, 3853-3858.
(Non-Patent Document 7)7. Environ. Sci. Technol., 2005, 39, 5095-5100.
(Non-Patent Document 8)8. Chem. Soc. Rev., 2011, 40, 3703-3727.
(Non-Patent Document 9)9. ACS Catal., 2013, 3, 2412-2416.
(Non-Patent Document 10)10. JACS, 2012, 134, 5500-5503.
(Non-Patent Document 11)11. Science, 2013, 342, 1382-1385.
(Non-Patent Document 12)12. JAGS, 2014, 136, 15473-15476.
(Non-Patent Document 13)13. Green Chem., 2016, 18, 5989-5993.
(Non-Patent Document 14)14. Green Chem., 2011, 13, 2285.
(Non-Patent Document 15)15. PNAS, 2008, 105, 10654-10658.
(Non-Patent Document 16)16. Bioresour. Technol., 2015, 185, 35-39.

DESCRIPTION OF EMBODIMENTS

Technical Problem

An aspect provides a recombinant microorganism for producing formate, from which an endogenous gene encoding formate dehydrogenase 1 alpha subunit (FDH1α) is deleted and into which an exogenous gene encoding formate dehydrogenase 1 (FDH1) is introduced.

Another aspect provides a method of producing formate, the method including culturing the microorganism in a medium.

Solution To Problem

Unless defined otherwise, all technical terms used herein have the same meanings as those generally understood by one of ordinary skill in the art to which the present disclosure belongs. Further, although methods or samples are described herein, those similar or equivalent thereto are also incorporated in the scope of the present disclosure. The contents of all the publications disclosed as references herein are incorporated in the present disclosure.

An aspect provides a recombinant microorganism for producing formate, from which an endogenous gene encoding formate dehydrogenase 1 alpha subunit (FDH1α) is deleted and into which an exogenous gene encoding FDH1 is introduced.

In a specific embodiment, the recombinant microorganism may be derived from a microorganism of the genus *Methylobacterium*.

In a specific embodiment, the microorganism of the genus *Methylobacterium* may be selected from the group consisting of *M. adhaesivum, M. aerolatum, M. aminovorans, M. aquaticum, M. brachiatum, M. brachythecii, M. bullatum, M. cerastii, M. chioromethanicum, M. dankookense, M. extorquens, M. fujisawaense, M. gnaphalii, M. goesingense, M. gossipiicola, M. gregans, M. haplocladii, M. hispanicum, M. iners, M. isbiliense, M. jeotgali, M. komagatae, M. longum, M. marchantiae, M. mesophilicum, M. nodulans, M. organophilum, M. oryzae, M. oxalidis, M. persicinum, M. phyllosphaerae, M. phyllostachyos, M. platani, M. podarium, M. populi, M. pseudosasae, M. pseudosasicola, M. radiotolerans, M. rhodesianum, M. rhodinum, M. salsuginis, M. soli, M. suomiense, M. tardum, M. tarhaniae, M. thiocyanatum, M. thuringiense, M. trifolii, M. variabile*, and *M. zatmanii*.

In a specific embodiment, the recombinant microorganism may be modified from the microorganism of the genus *Methylobacterium*, and the microorganism of the genus *Methylobacterium* may produce formate. The present inventors tested formate productivity of various microorganisms of the genus *Methylobacterium* in electrochemical reactions according to Example 2. As a result, it was confirmed that a number of the microorganisms of the genus *Methylobacterium* are able to produce formate (FIG. 10). Since these microorganisms have similar enzymes having formate productivity, it is expected that formate productivity at a similar level to that obtained by *Methylobacterium extorquens* may be obtained by modifying genes related to FDH1α and FDH1. The modification may be genetic modification. Specifically, modification of deleting the gene encoding FDH1α and introducing the exogenous gene encoding FDH1 may be applied to the microorganism. The microorganism of the genus *Methylobacterium* capable of producing formate may include FDH1α and/or FDH1, and may be used to produce formate.

In a specific embodiment, the microorganism of the genus *Methylobacterium* may be selected from the group consisting of *M. adhaesivum, M. chloromethanicum, M. suomiense, M. platani, M. soli*, and *M. extorquens*.

In a specific embodiment, the microorganism of the genus *Methylobacterium* may be *Methylobacterium extorquens*, specifically, *Methylobacterium extorquens* AM1.

In a specific embodiment, the recombinant microorganism may be a microorganism with Accession No. KCTC 13388BP.

According to Examples, when fdh1α which is the endogenous gene encoding FDH1α is knocked out and fdh1 which is the gene encoding FDH1 is reintroduced by transformation in *Methylobacterium extorquens* AM1, formate production is increased, as compared with a wild-type *Methylobacterium extorquens* AM1. Surprisingly, when the gene encoding fdh1 is transformed and artificially expressed in the wild-type *Methylobacterium extorquens* AM1 without knockout pretreatment, formate production as in the recombinant microorganism of the present disclosure may not be expected. Therefore, to expect increased formate production in *Methylobacterium extorquens* AM1, both of the deletion of the endogenous gene encoding FDH1a and the introduction of the exogenous gene encoding FDH1 are required.

The FDH1 protein of *Methylobacterium extorquens* AM1 may be composed of FDH1α and FDH1β. The FDH1α may include an amino acid sequence of SEQ ID NO: 1 (GenBank accession No. ACS42636.1) and the FDH1β may include an amino acid sequence of SEQ ID NO: 2 (GenBank accession No. ACS42635.1). Therefore, fdh1α which is the gene encoding FDH1α may encode a polypeptide including the amino acid sequence of SEQ ID NO: 1 and may include a polynucleotide sequence of SEQ ID NO: 3 (GenBank accession, CP001510.1:5169596-5172565, *Methylobacterium extorquens* AM1, complete genome), and fdh1β which is the gene encoding FDH1β may encode a polypeptide including the amino acid sequence of SEQ ID NO: 2 and may include a polynucleotide sequence of SEQ ID NO: 4 (CP001510.1: 5167825-5169543, *Methylobacterium extorquens* AM1, complete genome). Further, fdh1α which is the gene encoding FDH1α may include both polynucleotides of SEQ ID NOS: 3 and 4.

In a specific embodiment, the exogenous gene encoding FDH1 may be introduced into a microorganism via a genetic material carrier. The genetic material carrier may be a vector. The term "vector" means a DNA construct including a DNA sequence operably linked to a suitable control sequence capable of expressing DNA in an appropriate host. The vector may be a plasmid, a phage particle, or simply a latent genomic insert. When the vector is transformed into an appropriate host, it may be replicated or functioned regardless of a host genome, or in some cases, it may be integrated into a genome itself. A plasmid is a type that is most generally used as a vector. Thus, in the present disclosure, "plasmid" and "vector" may be occasionally used interchangeably with each other. The vector used in the present disclosure may include other types of vectors having functions equivalent to those known or to be known in the art.

In a specific embodiment, the vector may include a PmxaF promoter. The vector including the PmxaF promoter is well known to those skilled in the art, for example, pCM110. Since the recombinant microorganism of the present disclosure includes the PmxaF promoter, there is an advantage that a substance to be easily obtained and controlled, such as methanol, may be used to control an expression level of FDH1. As demonstrated in Examples, formate production is increased with increasing expression level of FDH1 exogenously introduced, and therefore, a recombinant microorganism having an appropriately controlled FDH1 expression level may have more excellent formate productivity than the wild-type. The vector may be any vector known to those skilled in the art, as long as it is suitable for introducing the exogenous gene into a cell (specifically, a microorganism). In a specific embodiment, the PmxaF promoter may include a polynucleotide sequence of SEQ ID NO: 5.

Unlike general microorganisms, the recombinant microorganism of the present disclosure may produce formate from carbon dioxide using electrochemically produced electrons without an expensive electron donor such as NADH. Therefore, a system capable of supplying electrons for an environment in which the recombinant microorganism of the present disclosure exists may be used in the production of formate, and the system may include, for example, an electric system where an electrode is introduced to directly flow an electric current from a battery, or an electrochemical (chemical battery) system where an electric current is generated by an oxidation-reduction reaction to supply electrons. Therefore, in a specific embodiment, the recombinant microorganism may be applied to either the electric system or the electrochemical system in order to produce formate.

In a specific embodiment, the electrochemical system may be culturing in an electrochemical carbon dioxide reduction system. The electrochemical carbon dioxide reduction system refers to a system capable of reducing carbon dioxide to formate by using the principle of a chemical battery. The electrochemical conversion technology has advantages that a carbon dioxide reduction reaction is possible at room temperature and atmospheric pressure, no chemicals are emitted because of mainly using water and carbon dioxide, the system is simple, and its modulation is easy. According to the electrochemical carbon dioxide reduction system, it is possible to produce formate from carbon dioxide without microorganisms. However, as demonstrated in FIG. 2, formate may not be sufficiently produced at a measurable concentration without the microorganism of the present disclosure, and the production amount of the microorganism of the present disclosure is remarkably larger than that of the wild-type. As illustrated in FIG. 8, the electrochemical carbon dioxide reduction system may include, for example, a cathode such as copper, graphite, carbon felt, and carbon fiber, and an anode such as platinum, and may further include a reference electrode such as Ag/AgCl. However, the electrochemical carbon dioxide reduction system may be modified in a manner well known to those skilled in the art, as needed.

In a specific embodiment, the amount of formate produced by the recombinant microorganism may be regulated by a methanol concentration. According to Examples, the recombinant microorganism of the present disclosure produced formate at the highest concentration of 26.6 mM for 21 hours, when the 2 v/v % methanol (based on a volume of a medium) was used as an inducer. Therefore, the methanol concentration may be 2.0 v/v % or more as an initial concentration. The methanol concentration may be determined at 2.0 v/v % to 10.0 v/v %, 2.0 v/v % to 8.0 v/v %, 2.0 v/v % to 6.0 v/v %, or 2.0 v/v % to 4.0 v/v considering the toxicity to the growth of the microorganism.

In a specific embodiment, the recombinant microorganism may be cultured or applied to the system in an environment in which tungstate is present at a concentration of more than 30 μM and less than 120 μM. According to Examples, the recombinant microorganism of the present disclosure did not show a specific increase in the formate productivity in an environment in which tungstate was present at a concentration of 30 μM. Further, the formate productivity was reduced in an environment in which tungstate was present at a concentration of 120 μM. The recombinant microorganism of the present disclosure produced 25.7 mM of formate for 21 hours in an environment in which tungstate was present at a concentration of about 60 μM, indicating remarkably increased formate productivity, as compared with those at other concentrations. Therefore, the recombinant microorganism may be cultured or applied to the system in an environment in which tungstate is present at a concentration of 40 μM to 110 μM, 50 μM to 100 μM, 50 μM to 90 μM, 50 μM to 80 μM, or 50 μM to 70 μM, or about 60 μM.

FDH1 is known to contain W-pterin guanidine dinucleotide instead of molybdenum (Mo) as its prosthetic group [17]. Specifically, FDH1α includes bis-tungstopterin guanine dinucleotide cofactor, three 4Fe4S clusters, and one 2Fe2S cluster. FDH1β retains flavin mononucleotide (FMN), NAD, and one 4Fe4S cluster [18]. Purified FDH1β at atmosphere may be successfully applied for the regeneration of NADH by utilizing methyl viologen (MV) as an artificial electron mediator in the electrochemical reduction system [19]. Generally, the solubility of tungsten is known to be much lower than that of molybdenum, and their chemical properties are known to be very similar, but it appears that microorganisms prefer one over the other as a specific transporter [22, 23]. According to Examples, the recombinant microorganism of the present disclosure had increased formate productivity in an environment in which, among various electron mediators, methyl viologen, ethyl viologen, or a combination thereof is present. Therefore, in a specific embodiment, the recombinant microorganism may be a recombinant microorganism having increased formate productivity in an environment in which methyl viologen, ethyl viologen, or a combination thereof is present.

A further surprising feature of the microorganism of the present disclosure is that it may very effectively produce formate using electrons supplied from the cathode, and it may be very stable to atmospheric oxygen (e.g., about 1 mg/L of dissolved oxygen). Among the known biocatalysts, some biocatalysts directly utilize electrons supplied from a cathode, but they are very unstable to oxygen. Thus, their practical application was not possible [15]. Therefore, the microorganism of the present disclosure may be practically applied to an actual industrial processes, and thus it may be very useful.

Another aspect provides a method of producing formate, the method including culturing the microorganism of the present disclosure in a medium.

As mentioned above, the microorganism of the present disclosure may be cultured in the electrochemical carbon dioxide reduction system in order to produce formate. Therefore, in a specific embodiment, the method may further include saturating the medium with carbon dioxide; and electrically or electrochemically treating the medium. Injection concentration and rate of carbon dioxide may be controlled, as needed. For example, $CO_2$ gas may be injected at a purging concentration of 99.999% and a rate of about 1 mL/s.

In a specific embodiment, the medium in the method may further include methanol. As mentioned above, the amount of formate produced by the recombinant microorganism of the present disclosure may be regulated by methanol. An appropriate concentration of methanol is the same as mentioned above.

In a specific embodiment, the medium in the method may further include tungsten. As mentioned above, an appropriate concentration of tungstate is important to optimize the amount of formate produced by the recombinant microorganism of the present disclosure. The appropriate concentration of tungstate is the same as mentioned above.

In a specific embodiment, the medium in the method may further include an electron mediator that transfers electrons to FDH1. The electron mediator may be methyl viologen, ethyl viologen, or a combination thereof.

Advantageous Effects of Disclosure

A recombinant microorganism for producing formate according to an aspect, from which an endogenous gene encoding formate dehydrogenase 1 alpha subunit (FDH1α) is deleted and into which an exogenous gene encoding FDH1 is introduced, may be applied to produce formate in an efficient and environmentally friendly manner, and it is possible to facilitate the spread of a novel and advanced method of producing formate throughout the related industries due to the characteristics of the microorganisms that are easy to culture and transport.

By the method of producing formate according to another aspect, the method including culturing the microorganism in a medium, it is possible to produce formate safely and efficiently without generating harmful chemical by-products.

MODE OF DISCLOSURE

Hereinafter, the present disclosure will be described in more detail.

Unless defined otherwise, all technical terms used herein have the same meanings as those generally understood by one of ordinary skill in the art to which the present disclosure belongs. Further, although methods or samples are described herein, those similar or equivalent thereto are also incorporated in the scope of the present disclosure. The numerical values described herein are considered to include the meaning of "about", unless otherwise specified. The contents of all the publications disclosed as references herein are incorporated in the present disclosure.

Example 1: Preparation of Recombinant Microorganism

Figure 1:
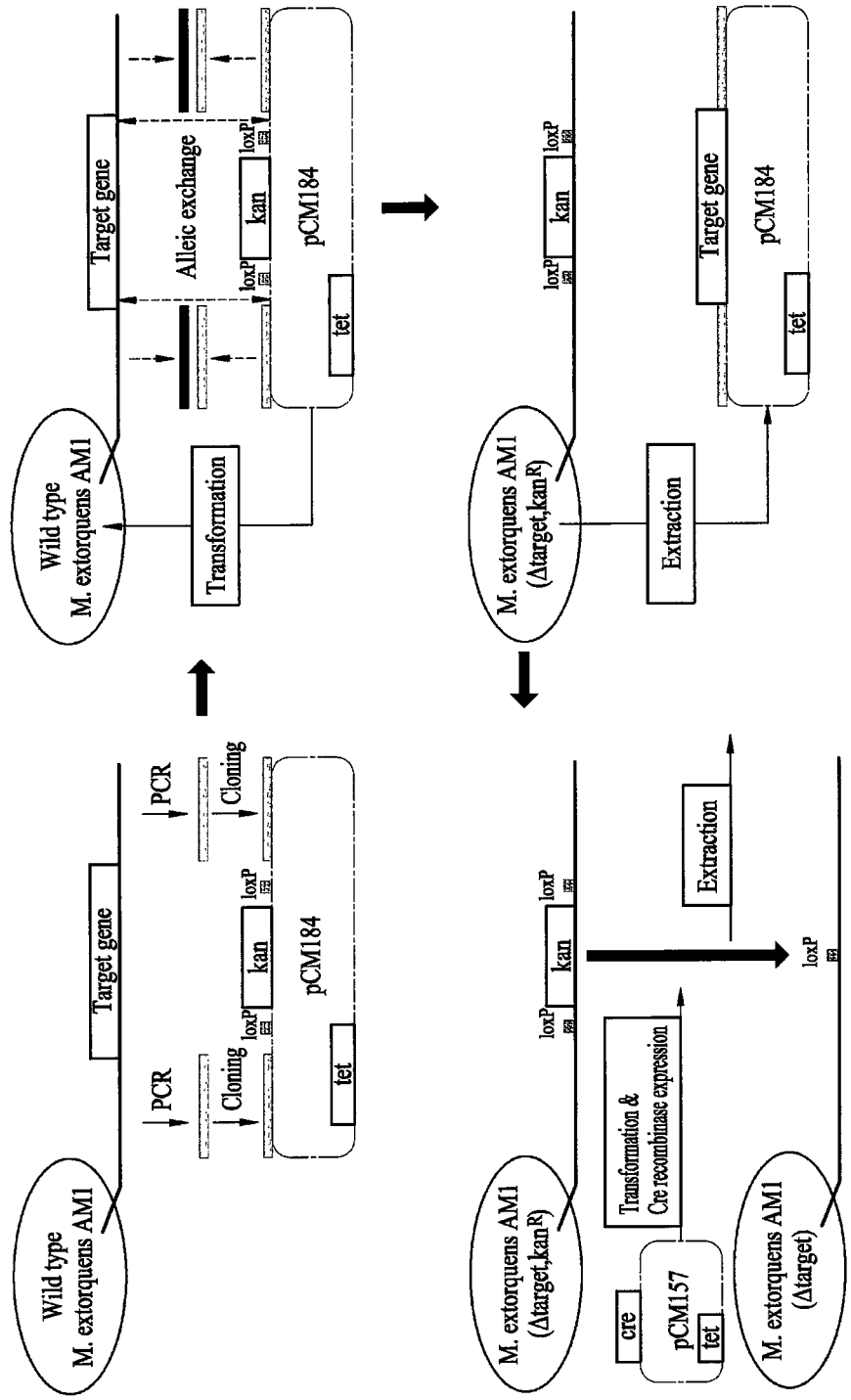
FIG. 1 illustrates a method of preparing mutant strains of *M. extorquens* AM1.

To prepare a recombinant microorganism, *Methylobacterium extorquens* AM1 (ATCC 14781, GenBank accession No. CP001510.1) was cloned and modified, as illustrated in FIG. 1. *Methylobacterium extorquens* AM1 is known to contain three formate dehydrogenase-coding genes (fdh1, fdh2, fdh3). Among the three formate dehydrogenase-coding genes, the fdh1 gene for FDH1 (GenBank accession No. ACS42636.1(α-subunit), ACS42635.1(β-subunit)) was selected to prepare the recombinant microorganism of *Methylobacterium extorquens* AM1, because it was reported to play an important role during whole-cell oxidation of formate [17].

For all the following cloning, one-step sequence and ligation-independent cloning (SLIC) was applied [25]. SLIC uses T4 DNA polymerase as exonuclease. This vector was linearized and amplified by restriction enzymes and a DNA amplifier. NEB 2.1 buffer (B7202S, BioLabs) and T4 polymerase were then added, and this mixture was incubated at room temperature for 2.5 min, then immediately incubated on ice for 10 min. Thereafter, 1 μl of the mixture was added to 100 μl of competent *E. coli* DH5α cells (RBC), and the DH5α cells were incubated on ice for 20 min. Then, 950 μl of LB medium was added and incubated at 37° C. for 16 hours.

A preparation procedure of the recombinant microorganism is as follows.

In detail, gene-knockout was performed according to a description of a paper [24]. First, according to the gene to be deleted, DNA located both upstream and downstream of FDH1α, and/or FDH1β gene (GenBank accession No. ACS42636.1(α-subunit), ACS42635.1(β-subunit)) of *Methylobacterium extorquens* AM1 was amplified. Primers used in the cloning are as in Table 1 below.

TABLE 1

| Primer | sequence |
|---|---|
| fdh1α knockout upstream F | 5'-gccgccatatgcatccatggtaccCCGGCGGGTCGATGCGGTTGGAAA-3' |
| fdh1α knockout upstream R | 5'-cacctgacgtctagatctg aattcTGGCCCGCGACCTCACCGCGAACTACTT-3' |
| fdh1α knockout downstream F | 5'-tggtcggctggatcctctagtgagctcTCTACGCCGAGGGCGTGAACGGACC-3' |
| fdh1α knockout downstream R | 5'-gatccagcttatcgataccgcgggcccGAGGTGCCGATAGGCGTGGCGCGA-3' |
| fdh1β knockout upstream F | 5'-gccgccatatgcatccatggtaccAATCTCTGTGTCCGCGCCT-3' |
| fdh1β knockout upstream R | 5'-cacctgacgtctagatctgaattcGCTTCACCGCGTTCTTGAGGAA-3' |
| fdh1β knockout downstream F | 5'-tggtcggctggatcctctagtgagctcGGCAGAGGTCTCGCCGTTGT-3' |
| fdh1β knockout downstream R | gatccagcttatcgataccgcgggcccGACGCGACCTGTGTTCCAACTAA-3' |

The amplified DNA was inserted to both sides of the loxP and kanamycin genes of pCM184 (Addgene plasmid 46012) and cloned. *Methylobacterium extorquens* AM1 was transformed with the cloned pCM184. When *Methylobacterium extorquens* AM1 is transformed with pCM184, allelic exchange occurs and *Methylobacterium extorquens* AM1 acquires loxP and kanamycin genes but loses a partial gene sequence of FDH1. The *Methylobacterium extorquens* AM1 was transformed with pCM157 (Addgene plasmid 45863), and the kanamycin gene between the loxP sites was extracted by site-specific recombination using the cre recombinase expressed from pCM157, to produce a knockout microorganism. Thereafter, the recombinant plasmid was expressed in the knockout microorganism, as needed. In detail, the specific gene-knockout *Methylobacterium extorquens* AM1 was transformed with pCM110 containing a gene encoding FDH1 or a gene encoding FDH1a to recover expression of FDH1 or FDH1a.

The following Table 2 shows bacterial strains and plasmids for knockout or for recombinant expression.

TABLE 2

| Strain | Deleted gene | Knockout plasmid | Recombinant plasmid | Selectable antibiotic |
|---|---|---|---|---|
| Wild-type | — | — | — | Rif |
| F1A | Δfdh1α | pCM184(Dfdh1α) | — | Rif, Kan |
| F1A-P1 | Δfdh1α | pCM184(Δfdh1α) pCM157(cre) | pCM110(fdh1) | Rif, Tet |
| F1AB-P1B | Δfdh1αβ | pCM184(Δfdh1α) pCM157(cre) pCM184(Δfdh1β) | pCM110(fdh1α) | Rif, Kan, Tet |

Among the prepared microorganisms, F1A-P1 was deposited under the terms of the Budapest Treaty at Korean Collection for Type Cultures, Korea Research Institute of Bioscience and Biotechnology, 181, Ipsin-gil, Jeongeup-si, Jeolllabuk-do 56212, Republic of Korea, on Nov. 10, 2017, with Accession No. KCTC 13388BP. A basic culture medium for the microorganisms included 16 g/L of succinate as a carbon source and a minimal salt medium (1.62 g/L $NH_4Cl$, 0.2 g/L $MgSO_4$, 2.21 g/L $K_2HPO_4$, and 1.25 g/L $NaH_2PO_4 \cdot 2H_2O$). As a selectable antibiotic to select the recombinant microorganisms, 50 pg/mL rifamycin (Rif), 50 pg/mL kanamycin (Kan), or 10 μg/mL tetracycline (Tet) was used. Each of the microorganisms was cultured in a 1 L Erlenmeyer shake flask with 200 mL volume at 26° C. and 200 rpm.

Example 2: Identification of Essential Enzymes for Production of formate from Carbon Dioxide Amounts of formate produced by the recombinant microorganisms prepared in Example 1 were measured under various conditions and compared.

As a formate production condition, an electrochemical carbon dioxide reduction system was used according to a previous paper [16]. The system includes a copper plate (2 cm×1.5 cm), a reference electrode (Ag/AgCl), and a platinum wire as an anode. In the system, the platinum wire generates both electrons and cations (e.g., protons) in a 1 mM sulfate aqueous solution (initial volume: 10 mL), and the generated cations pass through a proton-exchange membrane (Nafion®, 0.005-inch thickness, 30 cm×30 cm, Sigma-Aldrich, USA) to the cathode during carbon dioxide reduction reactions. The cathode section includes 0.6 g of wet-cell, 200 mM potassium phosphate buffer (pH 6.0), and 10 mM methyl viologen (MV) (initial volume: 10 mL), and worked to reduce carbon dioxide to formate by using electrons and cations supplied in the aqueous solution. For reduction reaction, the cathode section solution containing the microorganism was saturated with high purity carbon dioxide gas (99.999%, purging rate: 1 mL/s) and stirred at 300 rpm and room temperature. When the Ag/AgCl electrode (MF-2079, BASi) was used as a reference electrode, the electric potential (−0.75 V) of redox was constantly controlled by a potentiometer (MultiEnStat3, PalmSens, Netherlands), and the microorganism was cultured for an indicated time. Thereafter, the concentration of formate produced by whole-cell catalysis reaction was analyzed with HPLC. HPLC analysis was performed at 30° C. using a refractive index detector (RID) with an Aminex HPX 87-H Ion Exclusion Column (300 mm×7.8 mm, Bio-Rad) (mobile phase: 5 mM sulfuric acid, flow rate: 0.6 mL/min).

Figure 2:
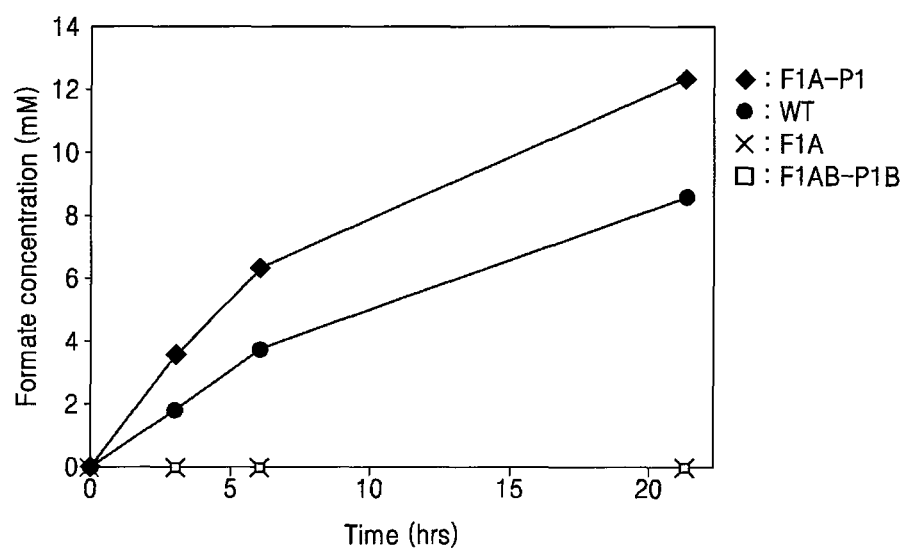
FIG. 2 is a graph showing formate production of various recombinant strains in an electrochemical reaction system (reaction conditions: 0.6 g wet-cell, 10 mM MV, pH 6.0; $CO_2$ gas purging, 99.999%, rate: 1 mL/s)

Results are shown in FIG. 2. As shown in FIG. 2, the wild-type and the recombinant microorganism F1A-P1 were able to produce formate from carbon dioxide in the electrochemical reduction system, but neither F1A which is a FDH1α knockout mutant nor F1AB-P1B which is an FDH1β knockout mutant produced any detectable level of formate. These results support that FDH1 is the key enzyme responsible for the conversion of carbon dioxide to formate, and both FDH1α and β are simultaneously required for FDH1 to function properly.

Further, formate productivity of F1A-P1 was 0.98 mM/hr/g-wet cell, and formate productivity of the wild-type was 0.68 mM/hr/g-wet cell, indicating that formate productivity of F1A-P1 is higher than that of the wild-type. The F1A-P1 strain is homologously expressed by a plasmid pCM10 (fdh1), which contains PmxaF as a strong inducible promoter. This promoter is able to significantly increase the expression of FDH1 because it has higher inducibility than other promoters [20]. Based on this result, it is supposed that FDH1 expression in cells may directly affect formate production.

Figure 9:
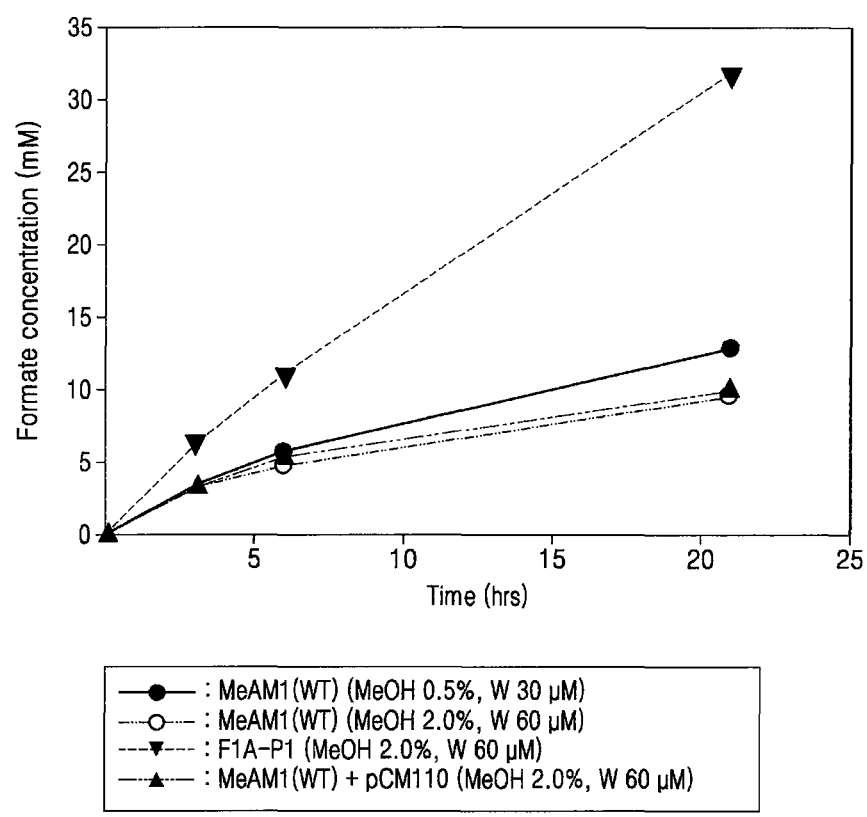
FIG. 9 shows formate concentrations for comparing formate productions of wild-type, F1A-P1, and wild-type+FDH1 under various conditions.

Further, fdh1 was transformed into the wild-type and overexpressed therein, as in Example 1, and then compared with F1A-P1. Surprisingly, when fdh1 was simply overexpressed (MeAM1(WT)+pCM110), it did not produce formate like F1A-P1 (FIG. 9).

Figure 10:
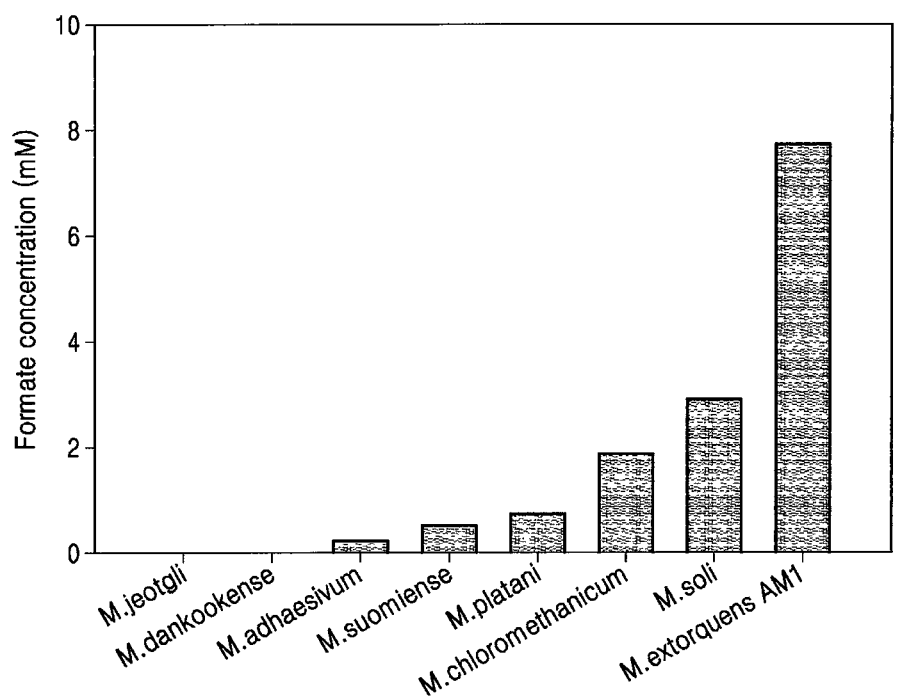
FIG. 10 shows formate productivity of various microorganisms of the genus Methylobacterium under electrochemical conditions.

Further, when the same electrochemical carbon dioxide reduction system was applied to various microorganisms of the genus *Methylobacterium*, many microorganisms were found to produce formate (FIG. 10).

Example 3: Confirmation of FDH1 Expression Level

Figure 3:
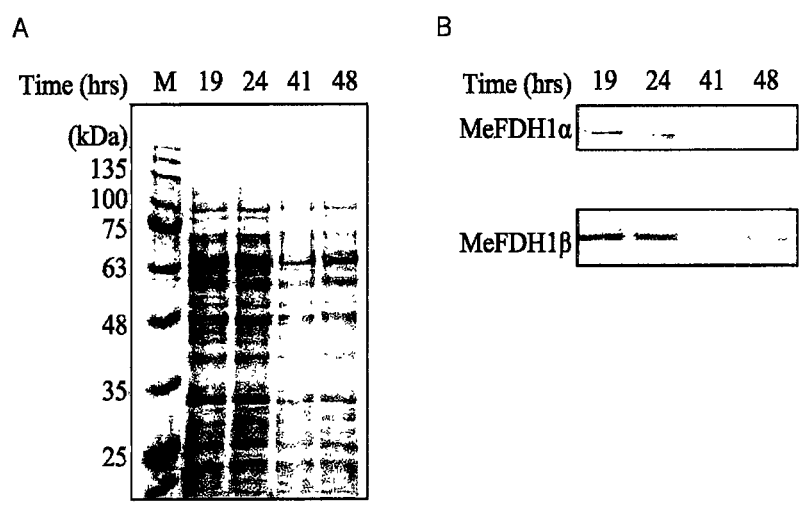
FIG. 3A shows a protein crude extract of a recombinant microorganism F1A-P1 loaded by SDS-PAGE (10%) and then stained with Coomassie blue (here, M indicates markers)
FIG. 3B shows Western blotting of FDH1α and FDH1β among proteins of the recombinant microorganism F1A-P1.

To analyze an FDH1 expression level of F1A-P1, polyacrylamide gel electrophoresis (SDS-PAGE) and Western blotting were performed. The target bands for FDH1α and FDH1β were difficult to distinguish by Coomassie blue staining due to their relatively weak expression in SDS-PAGE, despite molecular weight estimates of 108 kDa and 62 kDa, respectively (FIG. 3A). For this reason, Western blotting was further performed (FIG. 3B).

In detail, Western blotting was performed as follows. Microorganisms were lysed with a urea buffer (6 M urea, 200 mM NaCl, 20 mM Tris, pH 8.0), and an extract thereof was separated on SDS-PAGE (10% Tris/glycine). Thereafter, the resultant was transferred to a PVDF membrane (Cat. No. KDM20, 10 cm×10 cm, KOMA BIOTECH) through a semi-dry transfer (AE-8130, ATTA) with a transfer buffer (24.9 mM Tris, 2.5 M methanol, 191, 8 mM glycine, pH 8.4). Thereafter, the membrane was put in a blocking buffer (PBST; 10 mM phosphate buffer, 2.7 mM KCl, 137 mM NaCl, 1% (w/v) Tween 20) (2% (w/v) skim milk) and was incubated with gently shaking for 1 hour. The membrane was washed with a PBST buffer four times for 20 min and then transferred to a blocking buffer mixed with a primary antibody, and incubated with gently shaking for 1 hour. Next, the membrane was washed with a PBST buffer four times for 20 min, and then transferred to a blocking buffer mixed with a secondary antibody, and incubated with gently shaking for 1 hour. Finally, the membrane was washed with a BST buffer four times for 20 min, and then stained with a BCIP/NBT liquid substrate solution (B1911, SIGMA). For FDH1α, the primary antibody was Anti-6x His tag antibody (ab18184, ABCAM) (1:1000 dilution), and the secondary antibody was rabbit anti-mouse antibody (ab6729, ABCAM) (1:2000 dilution). For FDH1β, a customized primary antibody was used (ABFRONTIER) (1:1000 dilution), and the secondary antibody was goat anti-rabbit antibody (ab6722, ABCAM) (1:2000 dilution).

As a result, expression of FDH1α appeared decreased after incubation for 41 hours, even though the recovered expression level was observed repeatedly after incubation of F1A-P1 under basic culture conditions for 48 hours. These observations imply that a substantial proportion of homologously expressed recombinant FDH1 may be degraded through endogenous metabolism [21].

Example 4: Optimized Culture Conditions for Recombinant Microorganism

To obtain optimal conditions for producing formate from the recombinant microorganism, optimal culture conditions for recombinant microorganism were explored in the electrochemical carbon dioxide reduction system.

Microorganisms were cultured at 26° C. in a 200-rpm shaking incubator, and dissolved oxygen was maintained at about 1 mg/L. A culture medium for the microorganism was the basic culture medium used in Example 1, which was supplemented with trace elements (15 mg/L $Na_2EDTA_2HO$, 4.5 mg/L $ZnSO_4.7H_2O$, 0.3 mg/L $CoCl_2.6H_2O$, 1 mg/L $MnCl_2 4H_2O$, 1 mg/L $H_3BO_3$, 2.5 mg/L $CaCl_2$, 0.4 mg/L $Na_2MoO_4.2H_2O$, 3 mg/L $FeSO_4.7H_2O$, and 0.3 mg/L $CuSO_4.5H_2O$) and sodium tungstate, as needed. When methanol is added as an inducer, the culture medium was incubated for 19 hours, and then methanol was added thereto at indicated concentrations. Methanol may be used as an expression inducer and a carbon source for the recombinant microorganism F1A-P1, since expression of FDH1 is controlled by the methanol-inducible promoter PmxaF [20].

Figure 4:
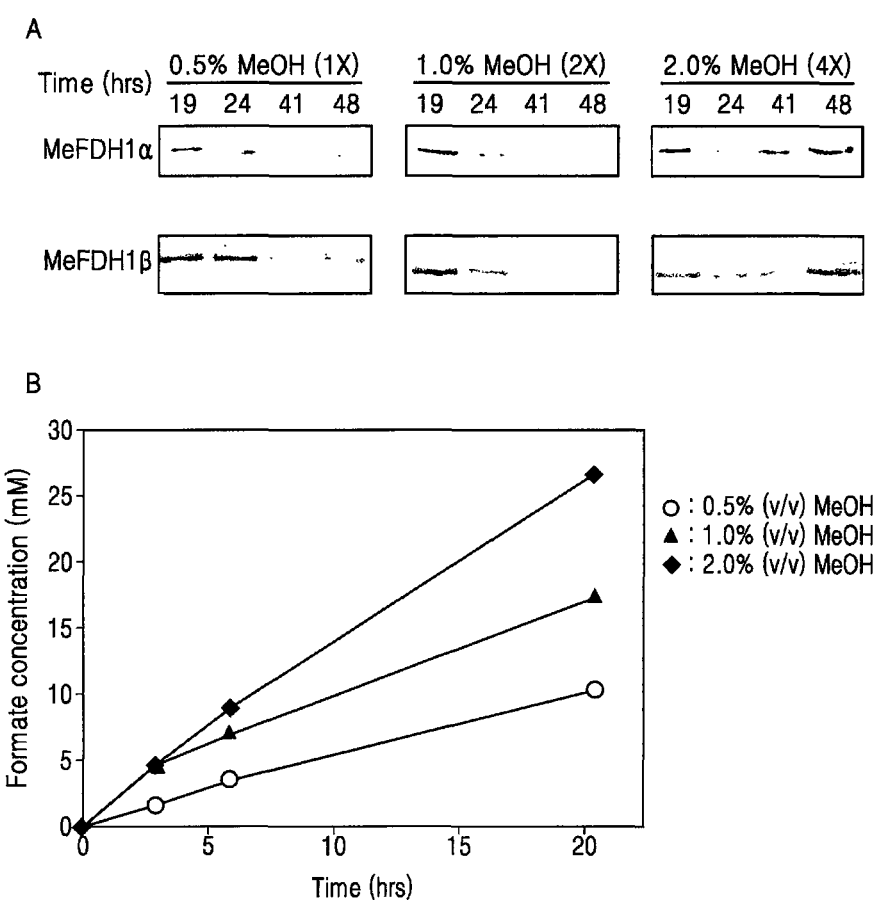
FIG. 4A shows Western blotting of FDH1α and FDH1β among proteins of the recombinant microorganism F1A-P1 at various concentrations of MeOH.
FIG. 4B is a graph showing formate production of the recombinant microorganism F1A-P1 at various concentrations of MeOH (reaction conditions: 0.6 g wet-cell, 10 mM MV, pH 6.0; $CO_2$ gas purging, 99.999%, rate: 1 mL/s)

As a result, it was observed that the methanol concentration in the medium affects FDH1 expression in F1A-P1, especially, after 48-hr incubation, the higher methanol concentration produces greater FDH1 expression in F1A-P1 (FIG. 4A). As predicted, the recombinant microorganism F1A-P1 cultured in the medium with methanol at an initial concentration of 2.0 v/v % based on the volume of the medium showed 2.11 mM-formate/hr/g-wet cell as the highest formate production rate in the electrochemical carbon dioxide reduction system (FIG. 4B).

Figure 5:
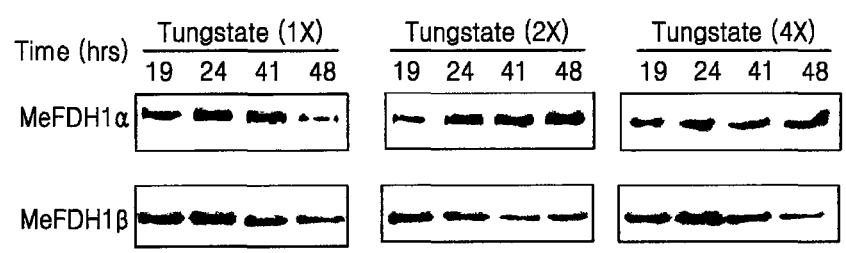
FIG. 5A shows Western blotting of FDH1α and FDH1β among proteins of the recombinant microorganism F1A-P1 at various concentrations of tungstate.
FIG. 5B is a graph showing formate production of the recombinant microorganism F1A-P1 at various concentrations of tungstate (reaction conditions: 0.6 g wet-cell, 10 mM MV, 0.5% (v/v) MeOH, pH 6.0; $CO_2$ gas purging, 99.999%, rate: 1 mL/s)
Figure 5:
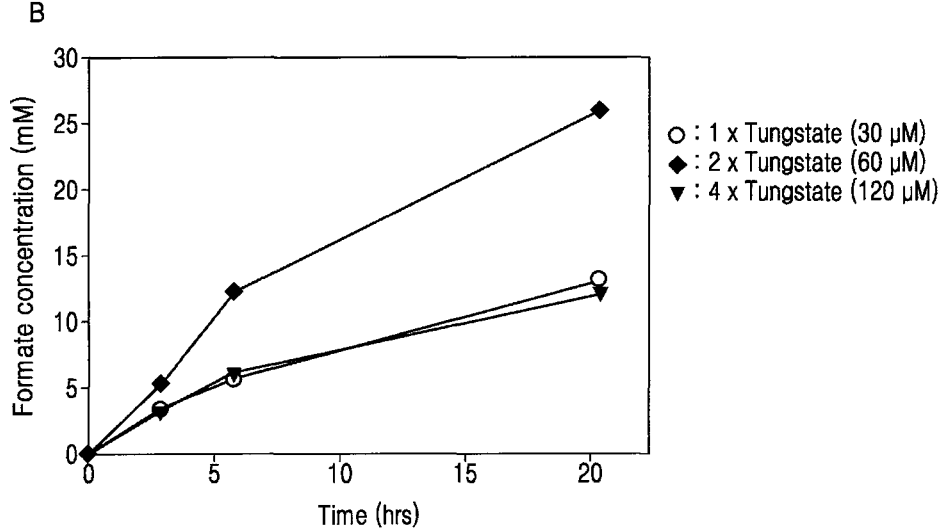

It was also observed that tungstate concentrations affect FDH1 expression in F1A-P1. According to FIG. 5, F1A-P1 cultured in 2x tungstate (60 µM) resulted in increased FDH1 expression and the highest formate productivity (FIG. 5B). However, F1A-P1 cultured in 4x tungstate (120 µM) showed no increase in the MeFDH1 expression (FIG. 5A). Interestingly, the optimum concentration of tungstate seems to repress FDH1 degradation (FIG. 5A), which implies that when tungstate is deficient, FDH1 apo-enzyme may be more vulnerable to endogenous degradation.

Figure 6:
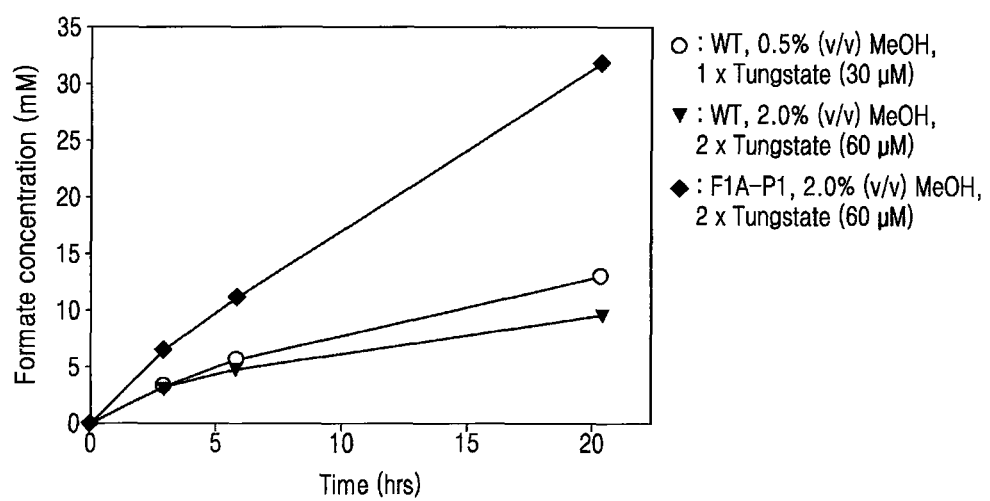
FIG. 6 is a graph showing formate production of the wild-type and the recombinant microorganism F1A-P1 under optimized conditions (reaction conditions: 0.6 g wet-cell, 10 mM MV, pH 6.0; $CO_2$ gas purging, 99.999%, rate: 1 mL/s)

Various combinations of methanol and tungstate conditions were used to compare formate productivity between the wild-type and F1A-P1. As a result, F1A-P1 produced over 30 mM of formate from carbon dioxide within 24 hours. This was three times greater than the production of the wild-type cultured at optimal methanol and tungstate concentrations (FIG. 6). It was also observed that optimal conditions did not greatly affect formate productivity of the wild-type *Methylobacterium extorquens* AM1. Furthermore, even though FDH1 was simply overexpressed in the wild-type, which was cultured in the optimal conditions of F1A-P1 (MeOH 2.0 v/v %, W(tungstate) 60 μM), the wild-type did not achieve the formate productivity of F1A-P1 (FIG. 9). This result demonstrates that although a genetic material including other promoters of the gene encoding FDH1 is used in the wild-type, it is difficult to obtain the same effect as in F1A-P1. Consequently, a promoter such as PmxaF was one of core factors for regulation of formate production of the recombinant microorganism F1A-P1 and for homologous expression of FDH1.

Figure 7:
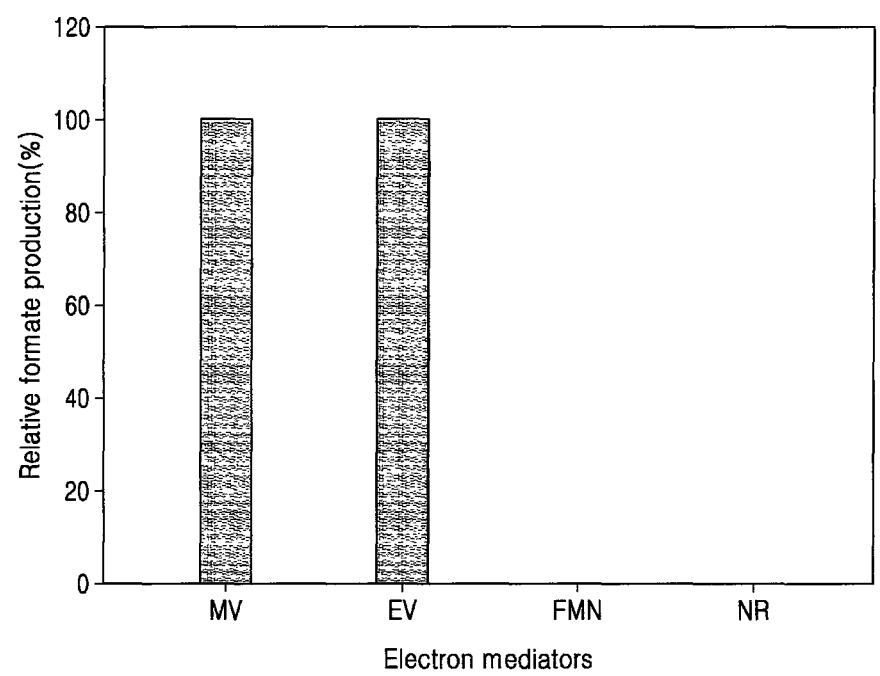
FIG. 7 shows a comparison of formate production of the recombinant microorganism F1A-P1 under culture conditions containing various electron mediators (MV; methyl viologen, EV; ethyl viologen, FMN; flavin mononucleotide, and NR; neural red)
Figure 8:
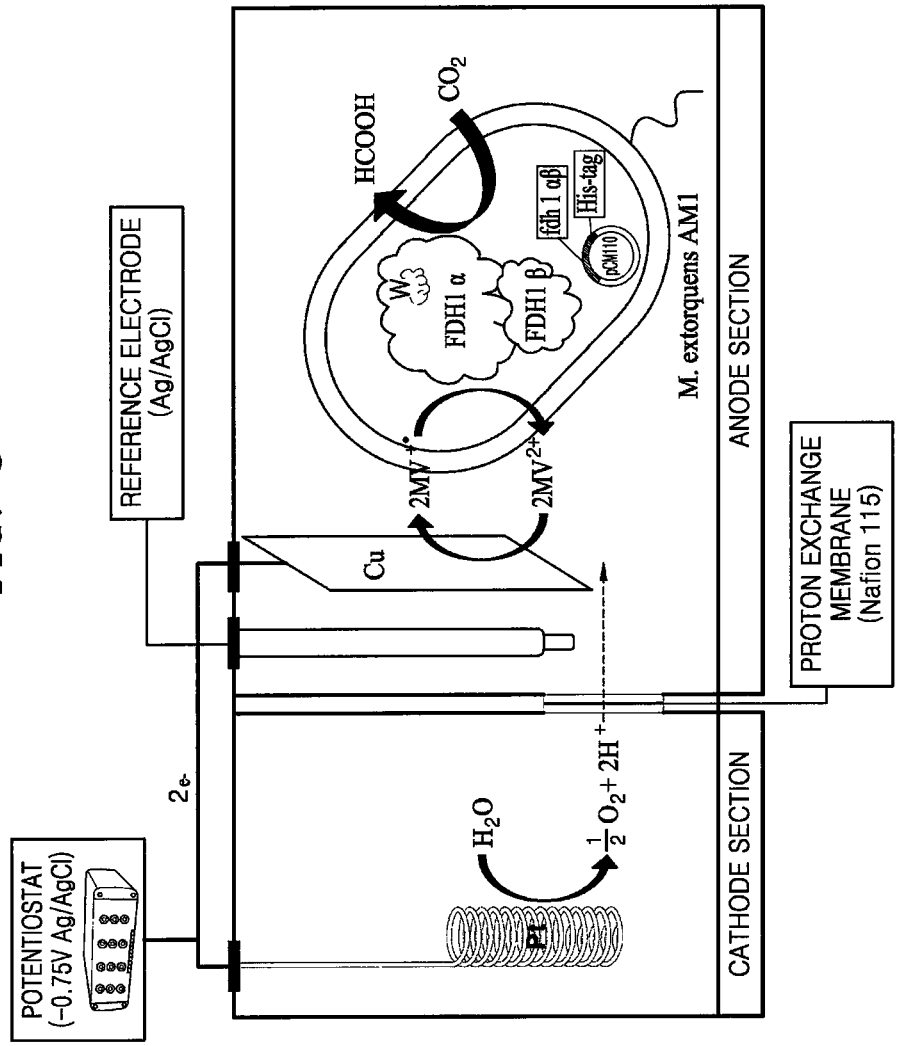
FIG. 8 illustrates an electrochemical carbon dioxide reduction system.

An artificial electron mediator is suitable for electron transfer from the copper plate cathode to FDH1 in the electrochemical carbon dioxide reduction system. Therefore, to determine whether F1A-P1 prefers a particular electron mediator, formate production was measured in environments in which many different electron mediators are present. As a result, it was confirmed that F1A-P1 could produce formate from carbon dioxide only when methyl viologen (MV) and ethyl viologen (EV) were employed as electron mediator (FIG. 7).

REFERENCE

1. S. J. Davis and K. Caldeira, PNAS, 2010, 107, 5687-5692.
2. S. Solomon, G. K. Plattner, R. Knutti and P. Friedlingstein, PNAS, 2009, 106, 1704-1709.
3. H. D. Matthews, N. P. Gillett, P. A. Stott and K. Zickfeld, Nature, 2009, 459, 829-U823.
4. M. Aresta, A. Dibenedetto and A. Angelini, Chem Rev, 2014, 114, 1709-1742.
5. A. Otto, T. Grube, S. Schiebahn and D. Stolten, Energy Environ. Sci., 2015, 8, 3283-3297.
6. T. Vo, K. Purohit, C. Nguyen, B. Biggs, S. Mayoral and J. L. Haan, ChemSusChem, 2015, 8, 3853-3858.
7. P. P. Hellsten, J. M. Salminen, K. S. Jorgensen and T. H. Nysten, Environ. Sci. Technol., 2005, 39, 5095-5100.
8. W. Wang, S. P. Wang, X. B. Ma and J. L. Gong, Chem. Soc. Rev., 2011, 40, 3703-3727.
9. C. A. Huff and M. S. Sanford, ACS Catal., 2013, 3, 2412-2416.
10. P. Kang, C. Cheng, Z. F. Chen, C. K. Schauer, T. J. Meyer and M. Brookhart, JACS, 2012, 134, 5500-5503.
11. K. Schuchmann and V. Muller, Science, 2013, 342, 1382-1385.
12. A. Bassegoda, C. Madden, D. W. Wakerley, E. Reisner and J. Hirst, JACS, 2014, 136, 15473-15476.
13. D. H. Nam, S. K. Kuk, H. Choe, S. Lee, J. W. Ko, E. J. Son, E. G. Choi, Y. H. Kim and C. B. Park, Green Chem., 2016, 18, 5989-5993.
14. F. Hollmann, I. W. C. E. Arends and D. Holtmann, Green Chem., 2011, 13, 2285.
15. T. Reda, C. M. Plugge, N. J. Abram and J. Hirst, PNAS, 2008, 105, 10654-10658.
16. H. Hwang, Y. J. Yeon, S. Lee, H. Choe, M. G. Jang, D. H. Cho, S. Park and Y. H. Kim, Bioresour. Technol., 2015, 185, 35-39.
17. L. Chistoserdova, M. Laukel, J. C. Portais, J. A. Vorholt and M. E. Lidstrom, J. Bacteriol., 2004, 186, 22-28.
18. T. Hartmann, N. Schwanhold and S. Leimkuhler, Biochim. Biophys. Acta., 2015, 1854, 1090-1100.
19. S. Lee, H. Choe, D. H. Cho, S. H. Yoon, K. Won and Y. H. Kim, J. Electrochem. Soc., 2016, 163, G50-G52.
20. C. J. Marx and M. E. Lidstrom, Microbiology, 2001, 147, 2065-2075.
21. A. Belle, A. Tanay, L. Bitincka, R. Shamir and E. K. O'Shea, PNAS, 2006, 103, 13004-13009.
22. J. J. G. Moura, C. D. Brondino, J. Trincao and M. J. Romao, J. Biol. Inorg. Chem., 2004, 9, 791-799.
23. Y. Zhang and V. N. Gladyshev, J. Mol. Biol., 2008, 379, 881-899.
24. C. J. Marx and M. E. Lidstrom, BioTechniques, 2002, 33, 1062-1067.
25. J. Y. Jeong, H. S. Yim, J. Y. Ryu, H. S. Lee, J. H. Lee, D. S. Seen and S. G. Kang, Appl. Environ. Microbiol., 2012, 78, 5440-5443.

Depository institution: Korea Research Institute of Bioscience and Biotechnology
Accession No: KCTC13388BP
Date of deposit: 20171110

The invention claimed is:

1. A recombinant microorganism comprising a genetic modification that increases production of formate, wherein the genetic modification comprises:
   a deletion of an endogenous gene encoding formate dehydrogenase 1 alpha subunit (FDH1α) and an introduction of an exogenous gene encoding a homologous formate dehydrogenase 1 (FDH1),
   wherein the recombinant microorganism is modified from a microorganism of the genus *Methylobacterium*, and the microorganism of the genus *Methylobacterium* produces formate,
   wherein the microorganism of the genus *Methylobacterium* is selected from the group consisting of *M. adhaesivum, M. chloromethanicum, M. suomiense, M. platani, M. soli*, and *M. extorquens*.

2. The recombinant microorganism of claim 1, wherein the microorganism of the genus *Methylobacterium* is *Methylobacterium extorquens*.

3. The recombinant microorganism of claim 1, wherein the recombinant microorganism is cultured in an electrical or electrochemical system.

4. The recombinant microorganism of claim 3, wherein the electrochemical system is an electrochemical carbon dioxide reduction system.

5. The recombinant microorganism of claim 1, wherein the exogenous gene is introduced by a vector.

6. The recombinant microorganism of claim 5, wherein the vector comprises a PmxaF promoter.

7. The recombinant microorganism of claim 1, wherein an amount of formate produced by the recombinant microorganism is regulated by a methanol concentration.

8. The recombinant microorganism of claim 1, wherein the recombinant microorganism is cultured in an environment in which tungstate is present at a concentration of more than 30 μM and less than 120 μM.

9. The recombinant microorganism of claim 1, wherein the recombinant microorganism is cultured in an environment in which methyl viologen, ethyl viologen, or a combination thereof is present.

10. The recombinant microorganism of claim 1, wherein the recombinant microorganism is Accession No. KCTC 13388BP.

11. A method of producing formate, the method comprising culturing the recombinant microorganism of claim 1 in a medium.

12. The method of claim 11, further comprising saturating the medium with carbon dioxide; and electrically or electrochemically treating the medium.

13. The method of claim 11, wherein the medium further comprises methanol.

14. The method of claim 11, wherein the medium further comprises tungsten.

15. The method of claim 11, wherein the medium further comprises an electron mediator that transfers electrons to FDH1.

* * * * *

SEQUENCE LISTING

<160> NUMBER OF SEQ ID NOS: 5

<210> SEQ ID NO 1
<211> LENGTH: 989
<212> TYPE: PRT
<213> ORGANISM: Methylobacterium extorquens

<400> SEQUENCE: 1

```
Met Ser Asn Gly Pro Glu Pro His Gly Asn Lys Ile Glu Gln Pro Glu
1               5                   10                  15

Ile Arg Ala Asp Glu Arg Gln Asp Ala Gly Gly Pro Ala Asn Gly Ala
            20                  25                  30

Pro Ser Thr Ser Gly Gly Ala Tyr Ser Gln Gly Ala Lys Ser Gly Gly
        35                  40                  45

Gln Ala Ala Pro Asp Pro Ser Gly Ser Tyr Gly Ile Lys Asp Ala Pro
    50                  55                  60

Val Ala Pro Ala Thr Ile Ala Phe Glu Phe Asp Gly Gln Gln Val Glu
65                  70                  75                  80

Ala Gln Pro Gly Glu Thr Ile Trp Ala Val Ala Lys Arg Leu Gly Thr
                85                  90                  95
```

His Ile Pro His Leu Cys His Lys Pro Asp Pro Gly Tyr Arg Pro Asp
            100                 105                 110

Gly Asn Cys Arg Ala Cys Met Val Glu Ile Glu Gly Glu Arg Val Leu
        115                 120                 125

Ala Ala Ser Cys Lys Arg Thr Pro Ala Ile Gly Met Lys Val Lys Ser
    130                 135                 140

Ala Thr Glu Arg Ala Thr Lys Ala Arg Ala Met Val Leu Glu Leu Leu
145                 150                 155                 160

Val Ala Asp Gln Pro Glu Arg Ala Thr Ser His Asp Pro Ser Ser His
                165                 170                 175

Phe Trp Val Gln Ala Asp Val Leu Asp Val Thr Glu Ser Arg Phe Pro
            180                 185                 190

Ala Ala Glu Arg Trp Thr Ser Asp Val Ser His Pro Ala Met Ser Val
        195                 200                 205

Asn Leu Asp Ala Cys Ile Gln Cys Asn Leu Cys Val Arg Ala Cys Arg
    210                 215                 220

Glu Val Gln Val Asn Asp Val Ile Gly Met Ala Tyr Arg Ala Ala Gly
225                 230                 235                 240

Ser Lys Val Val Phe Asp Phe Asp Asp Pro Met Gly Gly Ser Thr Cys
                245                 250                 255

Val Ala Cys Gly Glu Cys Val Gln Ala Cys Pro Thr Gly Ala Leu Met
            260                 265                 270

Pro Ala Ala Tyr Leu Asp Ala Asn Gln Thr Arg Thr Val Tyr Pro Asp
        275                 280                 285

Arg Glu Val Lys Ser Leu Cys Pro Tyr Cys Gly Val Gly Cys Gln Val
    290                 295                 300

Ser Tyr Lys Val Lys Asp Glu Arg Ile Val Tyr Ala Glu Gly Val Asn
305                 310                 315                 320

Gly Pro Ala Asn Gln Asn Arg Leu Cys Val Lys Gly Arg Phe Gly Phe
                325                 330                 335

Asp Tyr Val His His Pro His Arg Leu Thr Val Pro Leu Ile Arg Leu
            340                 345                 350

Glu Asn Val Pro Lys Asp Ala Asn Asp Gln Val Asp Pro Ala Asn Pro
        355                 360                 365

Trp Thr His Phe Arg Glu Ala Thr Trp Glu Glu Ala Leu Asp Arg Ala
    370                 375                 380

Ala Gly Gly Leu Lys Ala Ile Arg Asp Thr Asn Gly Arg Lys Ala Leu
385                 390                 395                 400

Ala Gly Phe Gly Ser Ala Lys Gly Ser Asn Glu Glu Ala Tyr Leu Phe
                405                 410                 415

Gln Lys Leu Val Arg Leu Gly Phe Gly Thr Asn Asn Val Asp His Cys
            420                 425                 430

Thr Arg Leu Cys His Ala Ser Ser Val Ala Ala Leu Met Glu Gly Leu
        435                 440                 445

Asn Ser Gly Ala Val Thr Ala Pro Phe Ser Ala Ala Leu Asp Ala Glu
    450                 455                 460

Val Ile Val Val Ile Gly Ala Asn Pro Thr Val Asn His Pro Val Ala
465                 470                 475                 480

Ala Thr Phe Leu Lys Asn Ala Val Lys Gln Arg Gly Ala Lys Leu Ile
                485                 490                 495

Ile Met Asp Pro Arg Arg Gln Thr Leu Ser Arg His Ala Tyr Arg His
            500                 505                 510

Leu Ala Phe Arg Pro Gly Ser Asp Val Ala Met Leu Asn Ala Met Leu

```
                515                 520                 525
Asn Val Ile Val Thr Glu Gly Leu Tyr Asp Glu Gln Tyr Ile Ala Gly
            530                 535                 540

Tyr Thr Glu Asn Phe Glu Ala Leu Arg Glu Lys Ile Val Asp Phe Thr
545                 550                 555                 560

Pro Glu Lys Met Ala Ser Val Cys Gly Ile Asp Ala Glu Thr Leu Arg
                565                 570                 575

Glu Val Ala Arg Leu Tyr Ala Arg Ala Lys Ser Ser Leu Ile Phe Trp
            580                 585                 590

Gly Met Gly Val Ser Gln His Val His Gly Thr Asp Asn Ser Arg Cys
                595                 600                 605

Leu Ile Ala Leu Ala Leu Ile Thr Gly Gln Ile Gly Arg Pro Gly Thr
            610                 615                 620

Gly Leu His Pro Leu Arg Gly Gln Asn Asn Val Gln Gly Ala Ser Asp
625                 630                 635                 640

Ala Gly Leu Ile Pro Met Val Tyr Pro Asp Tyr Gln Ser Val Glu Lys
                645                 650                 655

Asp Ala Val Arg Glu Leu Phe Glu Glu Phe Trp Gly Gln Ser Leu Asp
            660                 665                 670

Pro Gln Lys Gly Leu Thr Val Glu Ile Met Arg Ala Ile His Ala
                675                 680                 685

Gly Glu Ile Arg Gly Met Phe Val Glu Gly Glu Asn Pro Ala Met Ser
            690                 695                 700

Asp Pro Asp Leu Asn His Ala Arg His Ala Leu Ala Met Leu Asp His
705                 710                 715                 720

Leu Val Val Gln Asp Leu Phe Leu Thr Glu Thr Ala Phe His Ala Asp
                725                 730                 735

Val Val Leu Pro Ala Ser Ala Phe Glu Lys Ala Gly Thr Phe Thr
            740                 745                 750

Asn Thr Asp Arg Arg Val Gln Ile Ala Gln Pro Val Val Ala Pro Pro
            755                 760                 765

Gly Asp Ala Arg Gln Asp Trp Trp Ile Ile Gln Glu Leu Ala Arg Arg
            770                 775                 780

Leu Asp Leu Asp Trp Asn Tyr Gly Gly Pro Ala Asp Ile Phe Ala Glu
785                 790                 795                 800

Met Ala Gln Val Met Pro Ser Leu Asn Asn Ile Thr Trp Glu Arg Leu
                805                 810                 815

Glu Arg Glu Gly Ala Val Thr Tyr Pro Val Asp Ala Pro Asp Gln Pro
            820                 825                 830

Gly Asn Glu Ile Ile Phe Tyr Ala Gly Phe Pro Thr Glu Ser Gly Arg
            835                 840                 845

Ala Lys Ile Val Pro Ala Ala Ile Val Pro Pro Asp Glu Val Pro Asp
            850                 855                 860

Asp Glu Phe Pro Met Val Leu Ser Thr Gly Arg Val Leu Glu His Trp
865                 870                 875                 880

His Thr Gly Ser Met Thr Arg Arg Ala Gly Val Leu Asp Ala Leu Glu
                885                 890                 895

Pro Glu Ala Val Ala Phe Met Ala Pro Lys Glu Leu Tyr Arg Leu Gly
                900                 905                 910

Leu Arg Pro Gly Gly Ser Met Arg Leu Glu Thr Arg Arg Gly Ala Val
            915                 920                 925

Val Leu Lys Val Arg Ser Asp Arg Asp Val Pro Ile Gly Met Ile Phe
            930                 935                 940
```

```
Met Pro Phe Cys Tyr Ala Glu Ala Ala Asn Leu Leu Thr Asn Pro
945                 950                 955                 960

Ala Leu Asp Pro Leu Gly Lys Ile Pro Glu Phe Lys Phe Cys Ala Ala
            965                 970                 975

Arg Val Val Pro Ala Glu Ala Pro Met Ala Ala Glu
            980                 985

<210> SEQ ID NO 2
<211> LENGTH: 572
<212> TYPE: PRT
<213> ORGANISM: Methylobacterium extorquens

<400> SEQUENCE: 2

Met Ser Glu Ala Ser Gly Thr Val Arg Ser Phe Ala His Pro Gly Arg
1               5                   10                  15

Gly Arg Asn Val Ala Arg Ala Val Pro Lys Gly Arg Gln Val Asp Pro
                20                  25                  30

His Ala Lys Val Glu Ile Glu Glu Leu Leu Gly Thr Arg Pro Arg Gln
            35                  40                  45

Arg Asp Leu Leu Ile Glu His Leu His Leu Ile Gln Asp Thr Tyr Gly
        50                  55                  60

Gln Ile Ser Ala Asp His Leu Ala Ala Leu Ala Asp Glu Met Ser Leu
65                  70                  75                  80

Ala Phe Ala Glu Val Phe Glu Thr Ala Thr Phe Tyr Ala His Phe Asp
                85                  90                  95

Val Val Lys Glu Gly Glu Ala Asp Ile Pro Arg Leu Thr Ile Arg Val
            100                 105                 110

Cys Asp Ser Ile Thr Cys Ala Met Phe Gly Ala Asp Glu Leu Leu Glu
        115                 120                 125

Thr Leu Gln Arg Glu Leu Ala Ser Asp Ala Val Arg Val Val Arg Ala
130                 135                 140

Pro Cys Val Gly Leu Cys Asp His Ala Pro Ala Val Glu Val Gly His
145                 150                 155                 160

Asn Phe Leu His Arg Ala Asp Leu Ala Ser Val Arg Ala Ala Val Glu
                165                 170                 175

Ala Glu Asp Thr His Ala His Ile Pro Thr Tyr Val Asp Tyr Asp Ala
            180                 185                 190

Tyr Arg Ala Gly Gly Gly Tyr Ala Thr Leu Glu Arg Leu Arg Ser Gly
        195                 200                 205

Glu Leu Pro Val Asp Asp Val Leu Lys Val Leu Asp Asp Gly Gly Leu
210                 215                 220

Arg Gly Leu Gly Gly Ala Gly Phe Pro Thr Gly Arg Lys Trp Arg Ser
225                 230                 235                 240

Val Arg Gly Glu Pro Gly Pro Arg Leu Met Ala Val Asn Gly Asp Glu
                245                 250                 255

Gly Glu Pro Gly Thr Phe Lys Asp Gln Leu Tyr Leu Asn Thr Asp Pro
            260                 265                 270

His Arg Phe Leu Glu Gly Met Leu Ile Gly Ala His Val Val Glu Ala
        275                 280                 285

Ala Asp Val Tyr Ile Tyr Leu Arg Asp Glu Tyr Pro Ile Ser Arg Glu
        290                 295                 300

Ile Leu Ala Arg Glu Ile Ala Lys Leu Pro Glu Gly Gly Thr Arg Ile
305                 310                 315                 320

His Leu Arg Arg Gly Ala Gly Ala Tyr Ile Cys Gly Glu Glu Ser Ser
```

```
                    325                 330                 335
Leu Ile Glu Ser Leu Glu Gly Lys Arg Gly Leu Pro Arg His Lys Pro
                340                 345                 350
Pro Phe Pro Phe Gln Val Gly Leu Phe Asn Arg Pro Thr Leu Ile Asn
            355                 360                 365
Asn Ile Glu Thr Leu Phe Trp Val Arg Asp Leu Ile Glu Arg Gly Ala
        370                 375                 380
Glu Trp Trp Lys Ser His Gly Arg Asn Gly Arg Val Gly Leu Arg Ser
385                 390                 395                 400
Tyr Ser Val Ser Gly Arg Val Lys Glu Pro Gly Val Lys Leu Ala Pro
                405                 410                 415
Ala Gly Leu Thr Ile Gln Glu Leu Ile Asp Glu Tyr Cys Gly Gly Ile
                420                 425                 430
Ser Asp Gly His Ser Phe Ala Ala Tyr Leu Pro Gly Gly Ala Ser Gly
            435                 440                 445
Gly Ile Leu Pro Ala Ser Met Asn Asp Ile Pro Leu Asp Phe Gly Thr
        450                 455                 460
Leu Glu Lys Tyr Gly Cys Phe Ile Gly Ser Ala Ala Val Val Ile Leu
465                 470                 475                 480
Ser Asp Gln Asp Asp Val Arg Gly Ala Ala Leu Asn Leu Met Lys Phe
                485                 490                 495
Phe Glu Asp Glu Ser Cys Gly Gln Cys Thr Pro Cys Arg Ser Gly Thr
                500                 505                 510
Gln Lys Ala Arg Met Leu Met Glu Asn Gly Val Trp Asp Thr Asp Leu
            515                 520                 525
Leu Gly Glu Leu Ala Gln Cys Met Arg Asp Ala Ser Ile Cys Gly Leu
        530                 535                 540
Gly Gln Ala Ala Ser Asn Pro Val Ser Thr Val Ile Lys Tyr Phe Pro
545                 550                 555                 560
Asp Leu Phe Pro Glu Pro Arg Ala Val Ala Ala Glu
                565                 570
```

<210> SEQ ID NO 3
<211> LENGTH: 2970
<212> TYPE: DNA
<213> ORGANISM: Methylobacterium extorquens

<400> SEQUENCE: 3

```
atgagcaacg cccccgaacc gcacggcaac aagatcgaac agcccgagat ccgcgccgac      60
gaacgtcagg atgccggcgg ccggcaaat ggcgcaccat cgacctccgg cggcgcctac     120
tcgcagggcg ccaagtcggg tggccaggcc gcgccggatc cgtccggctc ctacggcatc     180
aaggacgccc cggtcgcgcc cgcgaccatc gccttcgagt cgacggcca acaggtcgag     240
gcccagcccg gcgagacgat ctgggcggtc gccaagcgcc ttggcacgca tatcccgcat     300
ctctgccaca gcccgatcc cggctaccgc ccggacggca attgccgcgc tgcatggtc      360
gagatcgagg gcgagcgcgt gctcgccgcc tcgtgcaagc gcacgcccgc catcggcatg     420
aaggtgaagt cggccaccga gcgcgccacc aaggcccgcg ccatggtgct cgaactgctc     480
gtggccgatc agcccgagcg cgcgacctcg catgacccgt cgtcgcattt ctgggtgcag     540
gccgacgtcc tcgatgtgac cgagagccgc ttcccggcgg ccgagcgctg gaccagcgac     600
gtcagccacc cggcgatgag cgtcaatctc gacgcctgca tccagtgcaa tctctgtgtc     660
cgcgcctgcc gcgaggttca ggtcaacgac gtgatcggca tggcctaccg cgccgcgggc     720
```

```
tccaaggtcg tgtttgactt cgacgatccg atgggtggct ccacctgcgt ggcctgcggc        780
gagtgcgtcc aagcctgccc gaccggggcg ctgatgccgg ccgcctatct cgacgcaaac        840
cagacccgga cggtctatcc cgaccgcgag gtgaagtcgc tctgcccta ttgcggcgtc         900
ggctgccaag tctcctacaa ggtcaaggac gagcgcatcg tctacgccga gggcgtgaac        960
ggaccggcca accagaaccg gctctgcgtg aagggccgct tcggcttcga ctacgtccac       1020
cacccccacc gcctgacggt gccgctgatc cgcttggaga acgtgcccaa ggacgccaac       1080
gatcaggtcg atccggcgaa ccctggacg catttccgcg aggcgacctg ggaagaggcg        1140
ctcgaccgcg cggcgggcgg cctgaaggcg atccgtgaca ccaacgggcg caaggcgctg       1200
gcgggcttcg gctcggccaa gggttcgaac gaggaggcct acctcttcca gaagctcgtc       1260
cgcctcggct tcggcaccaa caacgtcgat cactgcacgc gcctgtgcca cgcctcgtcg       1320
gtggcggcgc tgatggaggg cctgaattcc ggcgccgtca ccgctcccctt ctcggcagcg      1380
ctcgacgccg aggtcatcgt cgtcatcggc gccaacccga ccgtgaacca tccggtcgcg       1440
gcgaccttcc tcaagaacgc ggtgaagcag gcggcgcca agctgatcat catggacccg        1500
cggcgccaga cgctctcgcg ccacgcctat cggcacctcg ccttccgccc cggctcggac       1560
gtggcgatgc tcaacgcgat gctcaacgtg atcgtcacgg agggcctcta cgacgagcag       1620
tacatcgccg gctacaccga gaacttcgag gctctgcgcg agaagatcgt cgacttcacg       1680
ccggagaaga tggcctcggt ctgcggcatc gacgccgaga ccctgcgcga ggtcgcccgg       1740
ctctacgccc gggccaagtc gtcgctcatc ttctggggca tgggcgtcag ccagcacgtg       1800
cacggcaccg acaactcgcg ctgcctgatc gcgctcgccc tcatcaccgg ccagatcggc       1860
cggcccggca ccggcctgca cccgttgcgc ggccagaaca acgtccaggg cgcgtccgat       1920
gccggcctga tcccgatggt ctacccggac tatcagtcgg tcgagaagga cgcggtgcgt       1980
gagctgttcg aggagttctg ggggcagtcc ctcgatcctc agaagggcct caccgtggtc       2040
gagatcatgc gcgcgatcca cgcgggcgag atccggggca tgttcgtcga gggcgagaac       2100
ccggcgatgt ccgaccccga cctcaaccat gcccgccacg cgctggcgat gctcgaccat       2160
ctcgtggtgc aggacctgtt cctgacggag acggccttcc acgccgacgt ggtgctgccg       2220
gcctcggcct ttgccgagaa agccgggacc ttcaccaaca ccgaccggcg cgtgcagatc       2280
gcccagcccg tcgtcgcccc tccgggcgat gcgcgcagg attggtggat catccaggaa        2340
ctggcccgac gcctcgacct cgactggaac tacgcggcc cggccgacat cttcgccgag        2400
atggcgcagg tgatgccgtc cttgaacaac atcacctggg agcggctgga gcgcgagggg       2460
gcggtgacct atccggtcga tgccccggac cagcccggca acgagatcat cttctatgcc       2520
ggcttcccga ccgagagcgg tcgcgccaag atcgtgcccg cggcgatcgt gccgccggac       2580
gaggtgccgg acgacgagtt cccgatggtg ctctcgaccg gccgcgtgct cgaacactgg       2640
cacacgggct cgatgacccg gcgcgcgggc gtgctcgacg cgctggagcc ggaggcggtg       2700
gccttcatgg cacccaagga gctctaccgg ctcggtctcc ggcccggcgg gtcgatgcgg       2760
ttggaaacac ggcgcggcgc cgtcgtgttg aaggtgcgct ccgaccggga cgtgccgatc       2820
ggcatgatct tcatgccctt ctgctacgcg gaagccgccg ccaacttcct gaccaaccc       2880
gccctcgacc ccctcggaaa gattcccgag ttcaaattct gcgcagcccg cgtcgtcccc       2940
gcggaggctg cgccgatggc cgccgagtaa                                        2970

<210> SEQ ID NO 4
<211> LENGTH: 1719
```

```
<212> TYPE: DNA
<213> ORGANISM: Methylobacterium extorquens

<400> SEQUENCE: 4
atgagtgagg caagtgggac tgtccggagc ttcgcgcatc cgggccgtgg ccgtaacgtc      60
gcccgcgccg tgccgaaggg gcgtcaggtc gatcccacg ccaaggtcga gatcgaggag     120
ctgctcggca cccgcccgcg ccagcgcgac ctgctgatcg agcacctgca cctgatccaa    180
gacacctacg gccagatcag cgccgatcat ctcgcggcgc tggccgacga gatgagcctc    240
gccttcgccg aggtgttcga gaccgcgacc ttctacgcgc atttcgatgt ggtgaaggag    300
ggcgaggcca catcccgcg cctgacgatc cgggtttgcg acagcatcac ctgcgccatg     360
ttcggcgccg acgagctgct ggagacgctg cagcgcgagc tggcctcgga tgcggtccgc    420
gtcgtgcgcg cgcccgtgt cggcctgtgc gaccacgccc ggcggtcga ggtcgggcac     480
aacttcctgc accgggccga cctcgcctcc gtgcgcgccg cggtcgaggc cgaggacacc    540
cacgcccaca tccccactta cgtcgattac gacgcctacc gggccggcgg cggctacgcg    600
accctggagc ggctgcgcag cggcgaactg ccggtcgatg acgtgctgaa ggtgctcgac    660
gacggcggcc tgcgcggcct cggcggcgcc ggctttccca ccggccgcaa gtggcgctcc    720
gtgcgcggcg agcccggacc ccggctgatg gcggtcaacg cgacgaggg cgagcccggc    780
accttcaagg atcagctcta cctcaacacc gatccgcacc gctttctgga aggcatgctg    840
atcggcgccc acgtcgtcga ggccgccgac gtctacatct acctgcgcga cgagtacccg    900
atctcccgcg agatcctggc ccgcgagatc gcgaagctcc cgagggcgg cacccgcatc    960
cacctgcgcc gtggggccgg cgcctatatc tgcggcgagg aatcctcgct gatcgagtcg   1020
ctggagggca agcgcggcct gccgcggcac aagccgccct tccccttcca ggtcggcctg   1080
ttcaaccggc cgacgctgat caacaacatc gagacgctgt tctgggtgcg cgacctgatc   1140
gagcgcggcg ccgaatggtg gaagagccac gggcgcaacg gccgcgtcgg cctgcgctcg   1200
tactcggttt cgggccgggt caaggagccg ggcgtcaagc tcgcgcccgc cggcctgacc   1260
atccaggaac tcatcgacga gtattgcggc ggcatctctg acggccacag cttcgcggcc   1320
tacctgccgg gcggagcctc gggcggcatc ctgccggcct cgatgaacga catcccgctc   1380
gatttcggca cgctggaaaa ataccggctg ttcatcggct cggccgcggt cgtgatcctg   1440
tccgatcagg acgatgtgcg cggtgccgcg ttgaacctga tgaagttctt cgaggacgag   1500
tcctgcgggc agtgcacgcc ctgccgctcg ggcacgcaga aggcccgcat gctgatggag   1560
aacggcgtgt gggacaccga tctcctcggc gagctggcgc aatgcatgcg cgacgcctcg   1620
atctgcggtc tcggtcaggc ggcctcgaac ccgtcagca ccgtgatcaa gtacttccct    1680
gatctcttcc cggagccgcg ggccgtggcg gccgagtga                          1719

<210> SEQ ID NO 5
<211> LENGTH: 340
<212> TYPE: DNA
<213> ORGANISM: Artificial Sequence
<220> FEATURE:
<223> OTHER INFORMATION: PmxaF promoter

<400> SEQUENCE: 5
cgagggcccg ttgacgacaa cggtgcgatg ggtcccggcc ccggtcaaga cgatgccaat      60
acgttgcgac actacgcctt ggcactttta gaattgcctt atcgtcctga taagaaatgt    120
ccgaccagct aaagacatcg cgtccaatca aagcctagaa aatataggcg aagggacgct    180
```

```
                                      -continued aataagtctt tcataagacc gcgcaaatct aaaaatatcc ttagattcac gatgcggcac       240
ttcggatgac ttccgagcga gcctggaacc tcagaaaaac gtctgagaga taccgcggat       300
cctaagggcg aattccagca cactggcggc cgttactagt                             340
```